United States Patent [19]

Lim et al.

[11] Patent Number: 5,270,031
[45] Date of Patent: Dec. 14, 1993

[54] DENTINAL DESENSITIZING COMPOSITIONS

[75] Inventors: Richard M. Lim, Livingston; James K. Herms, Jersey City; Joseph Synodis, Summit, all of N.J.

[73] Assignee: Block Drug Company Inc., Jersey City, N.J.

[21] Appl. No.: 811,811

[22] Filed: Dec. 20, 1991

[51] Int. Cl.$^5$ .................. A61K 7/16; A61K 33/24
[52] U.S. Cl. ........................ 424/49; 424/48; 424/440; 424/449
[58] Field of Search ................... 424/49-58

[56] References Cited

U.S. PATENT DOCUMENTS

| | | | |
|---|---|---|---|
| 2,975,102 | 3/1961 | Matsumura et al. | 167/93 |
| 3,978,206 | 8/1976 | Naumann et al. | 424/49 |
| 4,296,096 | 10/1981 | Pierce | 424/52 |
| 4,847,070 | 7/1989 | Pyrz et al. | 424/52 |
| 4,871,531 | 10/1989 | Hartlaub et al. | |
| 4,906,456 | 3/1990 | Gaffar et al. | 424/52 |
| 4,931,273 | 6/1990 | Gaffar et al. | 424/52 |
| 4,933,171 | 6/1990 | Bristow et al. | 424/57 |
| 4,965,067 | 10/1990 | Wietfeldt | 424/52 |
| 4,992,258 | 2/1991 | Mason | 424/49 |
| 5,013,541 | 5/1991 | Elliott et al. | 424/52 |
| 5,015,466 | 5/1991 | Parran et al. | 424/52 |
| 5,015,467 | 5/1991 | Smitherman | 424/52 |
| 5,017,363 | 5/1991 | Suhonen | 424/52 |
| 5,032,386 | 7/1991 | Gaffar et al. | 424/49 |
| 5,087,444 | 2/1992 | Jackson et al. | 424/49 |
| 5,139,768 | 8/1992 | Friedman | 424/49 |
| 5,160,737 | 11/1992 | Friedman et al. | 424/49 |
| 5,188,818 | 2/1993 | Merianos et al. | |

FOREIGN PATENT DOCUMENTS

| | | | |
|---|---|---|---|
| 200508 | 12/1986 | European Pat. Off. | 514/902 |
| 278744 | 8/1988 | European Pat. Off. | 424/52 |
| 354447 | 2/1990 | European Pat. Off. | 424/52 |
| 390456 | 10/1990 | European Pat. Off. | 424/52 |

OTHER PUBLICATIONS

"Evaluation of Tartar Control Dentrifices in In Vitro Models of Dentin Sensitivity" by Dr. S. Mason et al., Clinical Preventive Dentistry, vol. 12, No. 6, Jan. 1991.

*Primary Examiner*—Shep K. Rose
*Attorney, Agent, or Firm*—Ostrelenk, Faber, Gerb & Soffen

[57] ABSTRACT

A composition containing a water soluble or water swellable polyelectrolyte or salts thereof in a dentifrice base or other oral compositions which can be used for relieving pain and discomfort caused by hypersensitive teeth. The salts can be single or mixed partial salts of the polyelectrolyte.

11 Claims, No Drawings

DENTINAL DESENSITIZING COMPOSITIONS

BACKGROUND OF THE INVENTION

Hypersensitive teeth can cause pain and discomfort when subjected to changes in temperature, pressure, or chemical action. Exposure of the dentin frequently leads to hypersensitivity. Dentin exposure may occur due to recession of the gums, periodontal disease and improper dental care. The usual method of treating hypersensitive teeth employs a desensitizing dentifrice or solution. Some of the active ingredients used in desensitizing dentifrices include strontium chloride, strontium acetate, potassium nitrate, and potassium chloride, other treatments are applied professionally as a solution. These include solutions of ferric oxalate or potassium oxalate.

One approach to desensitization is to occlude exposed dentinal tubules. Dentinal tubules lead from the pulp to the surface of the dentin. When the surface of the tooth is eroded, the dentinal tubules become exposed to the external environment. The exposed dentinal tubules provide a pathway for transmission of fluid flow to the pulpal nerves and this is induced by changes in temperature, pressure and ionic gradients. By blocking the tubules, the external stimuli have a diminished effect, and less pain will be felt.

Some active ingredients, such as ferric oxalate, are known to form mineral deposits on the surfaces of exposed dentinal tubules, effectively blocking the openings. In some cases, the abrasive action from brushing may cause a smear layer to form over the surface of the tooth and thus plug up the open tubules. The accumulation of particulate matter from the interstitial fluid passing through the dentinal tubules or remineralization within the tubules can cause a natural occlusion of the tubules.

Nerve inactivation is another mechanism whereby desensitization can occur. This relies on the action of an active ingredient such as potassium nitrate on the nerves. By altering the ionic balance in the nerve, the threshold of nerve stimulation is increased. Thus a higher level of stimulation is needed to evoke a painful response.

The materials which have been used as active ingredients in the treatment of hypersensitive teeth are generally inorganic salts or hydrophobic compounds. Although hydrophilic polymers have been used in oral compositions as excipients or the like, they have not been suggested as being useful active ingredients for desensitization purposes. Most of the hydrophilic polymers have been used to control the viscosity of the oral formulation or to give it thixotropic properties.

An example of such a polymer is polyacrylic acid which is used as a thickener in dentifrice formulations. It has also been used in gels, mouthwashes and buccal adhesive patches. However, polyacrylic acid has also been used for other purposes. For example, Leonard et al. (U.S. Pat. No. 5,011,830) state an oral composition containing an alkali pyrophosphate salt, a fluoride salt and a polyacrylic acid or a copolymer of acrylic acid and another monomer can provide enhanced anti-calculus benefits. Gaffar (U.S. Pat. No. 3,956,480) uses an anionic polymer such as polyacrylic acid with chlorhexidine as an anti-calculus agent. Benedict and Sunberg (U.S. Pat. No. 4,661,341) describe the use of polyacrylic acid or copolymers of polyacrylic acid as anti-calculus agents.

Another polymer which is used in oral compositions is the copolymer of methyl vinyl ether and maleic anhydride (MVE/MA) or the hydrolyzed acid copolymer. The MVE/MA copolymer and its salts have been used to enhance anti-calculus, anti-plaque, and anti-caries activity, and to control mouth odor. It has also been used to stabilize active agents in dentifrice formulations.

Suhonen (U.S. Pat. Nos. 4,960,586; 4,961,924) uses the MVE/MA copolymer to stabilize stannous fluoride dentifrice compositions.

Gaffar et al. (U.S. Pat. No. 4,138,477) use a zinc compound with the MVE/MA copolymer in a composition to control mouth odor and also to prevent calculus, caries, plaque, and periodontal disease.

Wietfeldt (U.S. Pat. No. 4,965,067) uses the MVE/MA copolymer, a soluble fluoride ion source, and a strontium ion source in a dentifrice composition. The polymer is said to stabilize the combination of strontium and fluoride in the composition which will form a precipitate without stabilization.

Friedman (EP 0381445) claims an oral composition with an anti-hypersensitivity agent such as strontium chloride in a hydrophobic polymer which can be applied to the teeth. The polymer matrix has an affinity for the teeth and acts as a matrix for the sustained release of the active ingredient. An example of a carrier used is ethyl cellulose with polyethylene glycol as a plasticizer.

Mason (U.S. Pat. No. 4,992,258) discloses the use of montmorillonite clay and a MVE/MA copolymer in a dentifrice formulation for the treatment of hypersensitive teeth. It is asserted in this patent that the MVE/MA copolymer increases the effectiveness of the montmorillonite clay.

In none of the examples above or elsewhere, as far as we are aware, are these polymers claimed to provide adesensitizing effect. Even in the Mason patent where a MVE/MA copolymer was used to increase the effectiveness of a desensitizing agent there is no attribution of such properties to the polymer.

Zinner et al., A New Desensitizing Dentrifice:- Preliminary Report, JADA, Vol. 95 pp. 982-985, November 1977 reports that a Pluronic F127 based dentrifice, with or without sodium citrate, had some desensitizing efficacy. Pluronic F127 is a non-ionic water soluble copolymer of ethylene oxide and propylene oxide.

It has now been determined that water soluble or water swellable polyelectrolytes, i.e. polymers with functional groups that are capable of bearing one or more charged groups in an aqueous solution have desensitizing properties.

It is accordingly the object of this invention to provide new dentinal desensitizing agents. This and other objects of the invention will become apparent to those skilled in this art from the following detailed description.

SUMMARY OF THE INVENTION

This invention relates to an oral composition and method which is useful for relieving pain and discomfort caused by hypersensitive teeth. More particularly, the invention relates to the use of a water soluble or water swellable polyelectrolyte or the partial salts thereof as a dental desensitization agent. The cations used to make the salt can include ammonium, alkylammonium, calcium, sodium, potassium, strontium, magnesium, zinc, aluminum, tin, iron, barium, lanthanum, titanium, bismuth and copper. The salts may contain single cations or mixed cations.

The polymer and its salts may be formulated into a dentifrice, gel, buccal adhesive patch, mouthwash, lozenge, or gum. Use of these oral compositions on a regular basis can provide relief from the pain and discomfort of hypersensitive teeth. The oral composition described above may also provide for a sustained release mode of action for the delivery of strontium or potassium ions from the water soluble or water swellable polyelectrolytes. The polyelectrolytes may also be used in conjunction with additional desensitizing agents such as strontium chloride or potassium nitrate in an oral composition.

DESCRIPTION OF THE INVENTION

In accordance with the present invention, a water soluble or water swellable polyelectrolyte is used as a dentinal desensitizing agent. The agent can be incorporated into a dentifrice, gel, mouthwash, lozenge, buccal adhesive patch, gum or the like. The water soluble or swellable polymers are generally polyelectrolytes, that is, polymers which bear one or more functional groups capable of bearing a charge in an aqueous medium. These polyelectrolytes can be anionic, cationic or amphoteric.

One example of an anionic functional group is the carboxylate group. This group is found in such polymers as polyacrylic acid, copolymers of acrylic acid and maleic acid, copolymers of methacrylic acid and acrylic acid, copolymers of alkyl vinyl ethers and maleic acid or anhydride, and the like. In the alkyl vinyl ether/-maleic acid or anhydride copolymers, the alkyl group generally contains 1 to about 10 carbon atoms and is most preferably a methyl group. The copolymer can be produced using procedures well known in the art or commercially available forms can be employed. For instance, the methyl vinyl ether/maleic anhydride copolymer can be obtained from International Specialty Products under the tradename Gantrez®—AN or as the hydrolyzed acid under the tradename Gantrez®—S. Polyacrylic acid can be obtained from B.F. Goodrich under the tradename Carbopol® or Noveon® as a cross-linked polyacrylic acid. Polyacrylic acid can also be obtained from Rohm and Haas under the tradename Acusol TM. These and other usable anionic polyelectrolytes are available from various other manufacturers. Another anionic functional group is the sulfonate group which is found for instance in sodium polystyrene sulfonate polymers.

The polyelectrolytes can contain cationic functional groups such as quaternized amines, imines, amides and alkyl ammonium groups. Examples include copolymers of vinyl pyrrolidone and dialkyl aminoalkyl methacrylates, chitosan, cationic celluloses and the like. A copolymer of vinyl pyrrolidone and dialkyl aminoalkyl methacrylate is available from International Specialty Products under the tradename Gafquat®. Chitosan is available under various tradenames from several companies.

Amphoteric polymers can also be used as a dentinal desensitizing agent. Examples include the aminoalkyl methacrylate and acrylates, copolymers of aminoalkyl acrylamides and acrylates, gelatin and the like.

The foregoing polymers are illustrative. The main criteria are that the polymer is water soluble or water swellable and contains functional groups capable of bearing a charge.

The commercially available polymers are produced over a range of molecular weights. Thus, for instance, Gantrez®—AN is available as a high molecular weight grade (Gantrez®—AN-179 MW=80,000) down to a low molecular weight grade (Gantrez® AN-119 MW=30,000). Similarly, Carbopol® and Noveon® are available in different grades with different rheological properties. The different grades range in molecular weight from 450,000 (907 type) to 4,000,000 (940 type). It is preferable to employ the highest molecular weight grade consistent with the viscosity of the formulation being prepared and concentration of the agent. The formulations will contain a desensitizing amount which is generally of from about 0.1% to 30% by weight of the polymer or its partial salts, with about 1-15% being preferred and about 2-12% most preferred. For any given concentration, viscosity generally increases with molecular weight and for any given molecular weight, viscosity generally increases with concentration.

The properties of some of these polymers may be modified to obtain the most advantageous properties by neutralization or partial neutralization. The cation may be present in the salts at about 20% to 100% equivalent mole ratio of the polymer. The preferred range is from about 40% to 90% equivalent of the polymer. The cations that can be used include ammonium, alkylammonium, calcium, sodium, potassium, strontium, zinc, aluminum, magnesium, tin, iron, barium, lanthanum, titanium, bismuth and copper. The cations can be used singly or as a mixture of different cations. These salts as such are well known in the art.

The salts of the copolymer can be made by making a solution of the polymer in water and then adding a metal salt such as the hydroxide, carbonate, bicarbonate, oxide, acetate, citrate, lactate or formate. The metal salt is preferably alkaline. The solution is stirred, with heating if necessary, until the polymer has dissolved. It will usually have a pH between about 3.5 and 9, depending on the amount of metal salt used. The salt solution can be directly incorporated into an aqueous oral composition. Alternatively, the solution can be evaporated to dryness to give a solid salt which can be milled to a fine powder, if desired, and incorporated into an oral composition.

The polymer or its salts can be formulated into a dentifrice, mouthwash, lozenge, buccal adhesive patch or gum using ingredients and procedures which are well known and commonly used in preparing these oral compositions. By way of example, without limitation, it is possible to incorporate a fluoride source into the oral composition. Of course, the ingredients used to make the above oral compositions should be compatible with the polymer and its salts. It is also possible to formulate the oral compositions in conjunction with additional desensitizing agents. Additional desensitizing agents include, without limitation, sodium fluoride, sodium silicofluoride, zinc chloride, formaldehyde, glycerin and silver nitrate. Additional desensitizing agents may also include potassium-containing compounds, such as potassium nitrate, as described in U.S. Pat. No. 3,863,006 and strontium-containing compounds, such as strontium chloride, as described in U.S. Pat. No. 3,122,483.

The polyelectrolytes have an affinity for the tooth surface and can maintain their presence over a period of time. During that period, the MVE/MA copolymer salts that contain potassium or strontium or other actives can slowly release the ions into the oral environment. This allows for a longer term availability of the actives for desensitization.

In order to further illustrate the present invention, various non-limiting examples are set forth below. In these examples, as throughout this specification and claims, all temperatures are in degrees centigrade and all parts and percentages are by weight unless otherwise indicated.

EXAMPLE 1

A dispersion of 156 g Gantrezs AN-169 (MW=67,000) in 1.8 liters of water was stirred vigorously with heating and a slurry of 133 g strontium hydroxide, octahydrate in 320 g of water was slowly added to the mixture. The mixture was heated to 90° C. whereupon it started to become clear. Then the solution was allowed to cool to 70° C. and stirred at that temperature for an additional 2 hours. A 9% solution of a strontium (50% equivalent) MVE/MA salt was thus obtained. This solution was used as is or was evaporated to dryness and then milled to a fine powder.

EXAMPLE 2

A 12% solution of a potassium (40% equivalent) salt of the MVE/MA copolymer was made using 156 g of Gantrez ® AN-169 and 45g of potassium hydroxide in 1.5 liters of water following the procedure in Example 1.

This solution was used to make a dentifrice using the following ingredients:

| INGREDIENT | % WEIGHT |
| --- | --- |
| 12% Solution of MVE/MA (40% equivalent potassium salt) | 60.3% |
| Sorbitol | 11.4% |
| Glycerin | 12.0% |
| Carboxymethyl cellulose | 2.4% |
| Diatomaceous earth | 10.1% |
| Sodium lauryl sulfate (SLS) | 0.6% |
| TiO2 | 1.0% |
| Fumed silica | 1.6% |
| Flavor and preservative | 0.6% |

The dentifrice was made by mixing the 12% solution of the partial potassium (40% equivalent) MVE/MA salt, sorbitol, glycerin, silia, SLS, and TiO2 together. After mixing, the carboxymethyl cellulose was added and blended into a homogeneous mixture.

EXAMPLE 3

A dentifrice was prepared from:

| INGREDIENT | % WEIGHT |
| --- | --- |
| 6% Solution of MVE/MA (80% equivalent sodium salt) | 60.3% |
| TiO2 | 1.0% |
| Sorbitol | 12% |
| Fumed silica | 1.6% |
| CaCO3 | 10.1% |
| Glycerin | 12% |
| Carboxymethyl cellulose | 2.4% |
| SLS | 0.6% |

The dentifrice is made in a manner similar to that described in Example 2.

EXAMPLE 4

A gel containing a sodium (80% equivalent) salt of polyacrylic acid was prepared from the following ingredients:

| INGREDIENT | % WEIGHT |
| --- | --- |
| Polyacrylic Acid | 2.9% |
| Sodium hydroxide | 1.3% |
| Glycerine | 21.0% |
| Potassium Nitrate | 5.0% |
| Water | 69.8% |

EXAMPLE 5

A dentifrice containing a 5% polyacrylic acid (80% equivalent sodium salt) was prepared from the following ingredients.

| INGREDIENT | % WEIGHT |
| --- | --- |
| Polyacrylic Acid | 4.0% |
| Sodium hydroxide | 1.8% |
| Glycerin | 20.0% |
| Potassium Nitrate | 5.0% |
| Silica | 3.9% |
| Pluronic F-87* | 2.5% |
| Flavors & Preservatives | 0.7% |
| Water | 62.1% |

*Copolymer of ethylene oxide and propylene oxide

EXAMPLE 6

A gel was prepared from the following ingredients:

| INGREDIENT | % WEIGHT |
| --- | --- |
| Gelatin Type A | 14.3% |
| Calcium chloride, dihydrate | 5.7% |
| Urea | 5.7% |
| Water | 74.3% |

The pH was adjusted to 6.7 using sodium hydroxide.

EXAMPLE 7

A desensitizing solution was made from the following ingredients.

| INGREDIENT | % Weight |
| --- | --- |
| Vinyl pyrrolidone/dimethylamino ethyl methacrylate copolymer | 5% |
| Sodium chloride | 0.6% |
| Water | 94.4% |

The pH was adjusted to 7.7.

EXAMPLE 8

A desensitizing gel was made from the following ingredients:

| INGREDIENT | % Weight |
| --- | --- |
| Chitosan lactate | 6% |
| Water | 94% |

The pH was adjusted to pH 5.

EXAMPLE 9

A desensitizing solution was made from the following ingredients:

| INGREDIENT | % Weight |
| --- | --- |
| Poly (dimethyl diallyl-ammonium chloride) | 6% |
| Sodium Chloride | 0.6% |
| Water | 93.4% |

TESTS OF ORAL COMPOSITIONS OF EXAMPLES 1-9

The prepared solutions and oral compositions were tested using the method described by Pashley (J. Periodontology, Vol. 55, No. 9, p. 522, Sept. 1984). This test measures the flow of fluid through a sliced dentin disc. A treatment that will reduce the flow through the discs can also result in reduced dentinal hypersensitivity for people using the treatment.

A caries free tooth is sliced to obtain a 0.4 to 0.6 mm thick dentin disc. The disc is mounted on a split chamber device (J. Dent. Research 57:187, 1978). The initial flow of fluid through the disc is measured, and then the disc is treated by brushing with one of the desensitizing treatments. After brushing, the flow rate is again measured and the reduction in flow is calculated from these measurements. The following compositions were used and the reduction in flow is reported. The results for the dentifrices are based on 1 to 1 dilution with artificial or human saliva.

| Treatment | % Change in Flow |
| --- | --- |
| Example 1 | −43% |
| Example 2 | −47% |
| Example 3 | −39% |
| Example 4 | −48% |
| Example 5 | −63% |
| Example 6 | −57% |
| Example 7 | −80% |
| Example 8 | −69% |
| Example 9 | −59% |

EXAMPLE 10

A mouthwash was made by mixing the following ingredients:

| INGREDIENT | % WEIGHT |
| --- | --- |
| 10.3% solution of MVE/MA (90% equivalent sodium salt) | 70% |
| Alcohol 190 Proof (Grain Alcohol) | 10% |
| Pluronic F-127 | 2% |
| Flavor | 0.3% |
| Menthol | 0.02% |
| Water | q.s. to 100% |

EXAMPLE 11

The following composition was used to make a chewing gum:

| INGREDIENT | % WEIGHT |
| --- | --- |
| Chewing gum NOVA Base "A" | 24.64% |
| Glycerin | 1% |
| Calcium saccharin | 0.06% |
| Sorbitol powder | 53.5% |
| Lycasin | 13% |
| Lecithin | 0.8% |
| Flavor | 1% |
| Chitosan lactate | 6% |

The chewing gum base was softened at 65° C. using a sigma blade mixer, cooled to 60° C. and 3/5 of the sorbitol powder and calcium saccharin added, followed by the glycerin. Then 1/5 of the sorbitol powder, ½ of the lycasin and the chitosen were added. After cooling to 50° C., the rest of the sorbitol powder, lycasin, and flavor were added. The mixture was rolled into patties and cut into strips.

EXAMPLE 12

The following composition was used to make a lozenge:

| INGREDIENT | % WEIGHT |
| --- | --- |
| Sorbitol | 86.5% |
| Xylitol | 6% |
| Citric Acid | 0.4% |
| Flavor | 0.1% |
| Gelatin | 7% |

The sorbitol and xylitol were heated at 165° C. until the base started to thicken. The combination was cooled to 140° C. and the citric acid added. After cooling to 100° C., the gelatin was added and after cooling to 850° C., the flavor was added. Cooling was continued and a seed crystal of sorbitol was added to start crystallization. The mixture was poured into molds to form lozenges.

Various changes and modifications can be made in the process and products of this invention without departing from the scope thereof. The various embodiments described herein were for the purpose of further illustrating the invention but were not intended to limit it.

What is claimed is:

1. In a method of desensitizing teeth by applying thereto a desensitizing amount of an oral composition containing a desensitizing agent, the improvement which comprises employing as the desensitizing agent, at least one water soluble or water swellable polyelectrolyte which is polyacrylic acid salt having a degree of neutralization from about 20 to 100%.

2. The method of desensitizing teeth of claim 1 in which the polyelectrolyte cation is selected from the group consisting of ammonium, alkylammonium, calcium, sodium, potassium, strontium, zinc, aluminum, manganese, tin, iron, barium, lanthanum, titanium, bismuth and copper.

3. The method of desensitizing teeth of claim 2 in which the cation is sodium, calcium, potassium or strontium.

4. The method of desensitizing teeth in claim 1 in which said oral composition further comprises an additional desensitizing agent.

5. The method of desensitizing teeth of claim 1 in which the oral composition is in the form of a dentrifice.

6. The method of desensitizing teeth of claim 1 in which the oral composition is in the form of a mouthwash, gel, chewing gum, lozenge or buccal adhesive patch.

7. The method of desensitizing teeth of claim 1 in which the amount of desensitizing agent is about 0.1 to 30% by weight of the composition.

8. The method of desensitizing teeth of claim 10 in which the amount is about 1 to 15% by weight.

9. The method of desensitizing teeth of claim 11 in which the amount is about 2 to 12% by weight.

10. The method of desensitizing teeth of claim 1 in which the cation is potassium or strontium.

11. The method of desensitizing teeth of claim 1 in which the polyelectrolyte is water swellable and is a salt of polyacrylic acid having molecular weight of 450,000 to 4,000,000 and a degree of neutralization of about 40 to 90%.

* * * * *